(12) United States Patent
Esenaliev et al.

(10) Patent No.: US 7,430,445 B2
(45) Date of Patent: Sep. 30, 2008

(54) NONINVASIVE BLOOD ANALYSIS BY OPTICAL PROBING OF THE VEINS UNDER THE TONGUE

(75) Inventors: Rinat O. Esenaliev, League City, TX (US); Donald S. Prough, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 97 days.

(21) Appl. No.: 10/554,149

(22) PCT Filed: Apr. 26, 2004

(86) PCT No.: PCT/US2004/012758

§ 371 (c)(1),
(2), (4) Date: Oct. 21, 2005

(87) PCT Pub. No.: WO2004/096082

PCT Pub. Date: Nov. 11, 2004

(65) Prior Publication Data

US 2006/0195021 A1    Aug. 31, 2006

Related U.S. Application Data

(60) Provisional application No. 60/465,134, filed on Apr. 24, 2003.

(51) Int. Cl.
  *A61B 5/1455* (2006.01)
(52) U.S. Cl. ............... 600/344; 600/310; 600/322; 600/340
(58) Field of Classification Search ........ 600/310, 600/322, 323, 340, 344
See application file for complete search history.

(56) References Cited

U.S. PATENT DOCUMENTS

| | | | |
|---|---|---|---|
| 4,028,933 A | | 6/1977 | Lemons et al. |
| 4,167,331 A | * | 9/1979 | Nielsen ............... 600/322 |
| 4,212,206 A | | 7/1980 | Hartemann et al. |
| 4,255,971 A | | 3/1981 | Rosencwaig |
| 4,267,732 A | | 5/1981 | Quate |
| 4,385,634 A | | 5/1983 | Bowen et al. |
| 4,430,897 A | | 2/1984 | Quate |
| 4,594,662 A | | 6/1986 | Devaney |
| 4,710,030 A | | 12/1987 | Tauc et al. |
| 4,727,420 A | | 2/1988 | Kohda et al. |
| 4,890,619 A | * | 1/1990 | Hatschek ............. 600/323 |
| 4,953,539 A | | 9/1990 | Nakamura et al. |
| 4,971,991 A | | 11/1990 | Umemura et al. |
| 5,041,121 A | | 8/1991 | Wondrazek et al. |
| 5,136,172 A | | 8/1992 | Nakata et al. |
| 5,141,331 A | | 8/1992 | Oehler et al. |
| 5,158,560 A | | 10/1992 | Sogawa et al. |
| 5,161,125 A | | 11/1992 | Maccabee |
| 5,178,836 A | | 1/1993 | Kitamori et al. |
| 5,190,039 A | * | 3/1993 | Takeuchi et al. ........ 600/323 |
| 5,207,672 A | | 5/1993 | Roth et al. |

(Continued)

*Primary Examiner*—Eric F Winakur
(74) *Attorney, Agent, or Firm*—Robert W Strozier

(57) ABSTRACT

A method for analysis of blood components or parameters is disclosed where a probe having an excitation outlet and a response inlet is placed in proximity to or in contact with a tissue of an underside of a patient's tongue over a big vein in the tongue so that an excitation signal exits the outlet, produces a response which enters the inlet for detection and analysis.

13 Claims, 19 Drawing Sheets

U.S. PATENT DOCUMENTS

| | | |
|---|---|---|
| 5,254,112 A | 10/1993 | Sinofsky et al. |
| 5,293,873 A | 3/1994 | Fang |
| 5,341,805 A * | 8/1994 | Stavridi et al. ............. 600/316 |
| 5,348,002 A | 9/1994 | Caro |
| 5,348,003 A * | 9/1994 | Caro ......................... 600/310 |
| 5,349,954 A | 9/1994 | Tiemann et al. |
| 5,380,411 A | 1/1995 | Schlief |
| 5,398,685 A | 3/1995 | Wilk et al. |
| 5,403,590 A | 4/1995 | Forse |
| 5,417,653 A | 5/1995 | Sahota et al. |
| 5,421,337 A | 6/1995 | Richard-Kortum et al. |
| 5,444,541 A | 8/1995 | Small et al. |
| 5,465,722 A | 11/1995 | Fort et al. |
| 5,474,765 A | 12/1995 | Thorpe |
| 5,487,390 A | 1/1996 | Cohen et al. |
| 5,494,031 A * | 2/1996 | Hoeft ......................... 600/317 |
| 5,543,158 A | 8/1996 | Gref et al. |
| 5,554,810 A | 9/1996 | Anifrani et al. |
| 5,565,215 A | 10/1996 | Gref et al. |
| 5,578,325 A | 11/1996 | Domb et al. |
| 5,582,578 A | 12/1996 | Zhong et al. |
| 5,583,634 A | 12/1996 | Andre et al. |
| 5,588,428 A | 12/1996 | Smith et al. |
| 5,596,986 A | 1/1997 | Goldfarb |
| 5,599,712 A | 2/1997 | Greenberger |
| 5,602,894 A | 2/1997 | Bardash |
| 5,614,502 A | 3/1997 | Flotte et al. |
| 5,615,675 A | 4/1997 | O'Donnell et al. |
| 5,651,986 A | 7/1997 | Brem et al. |
| 5,662,590 A | 9/1997 | De La Torre et al. |
| 5,710,630 A | 1/1998 | Essenpreis et al. |
| 5,713,356 A | 2/1998 | Kruger |
| 5,718,231 A | 2/1998 | Dewhurst et al. |
| 5,722,406 A | 3/1998 | Papaioannou |
| 5,836,905 A | 11/1998 | Lemelson et al. |
| 5,840,023 A | 11/1998 | Oraevsky et al. ............ 600/407 |
| 5,897,494 A | 4/1999 | Flock et al. |
| 5,902,237 A | 5/1999 | Glass |
| 5,924,986 A | 7/1999 | Chandler et al. |
| 5,944,687 A | 8/1999 | Benett et al. |
| 5,977,538 A | 11/1999 | Unger et al. |
| 6,049,728 A | 4/2000 | Chou |
| 6,064,898 A | 5/2000 | Aldrich |
| 6,125,290 A | 9/2000 | Miesel |
| 6,165,440 A | 12/2000 | Esenaliev .................. 424/1.11 |
| 6,175,759 B1 | 1/2001 | Chan et al. |
| 6,309,352 B1 | 10/2001 | Oraevsky et al. ............ 600/407 |
| 6,485,413 B1 | 11/2002 | Boppart et al. |
| 6,498,942 B1 | 12/2002 | Esenaliev et al. ........... 600/310 |
| 6,725,073 B1 | 4/2004 | Motamedi et al. ........... 600/316 |
| 6,751,490 B2 | 6/2004 | Esenaliev et al. ........... 600/310 |

\* cited by examiner

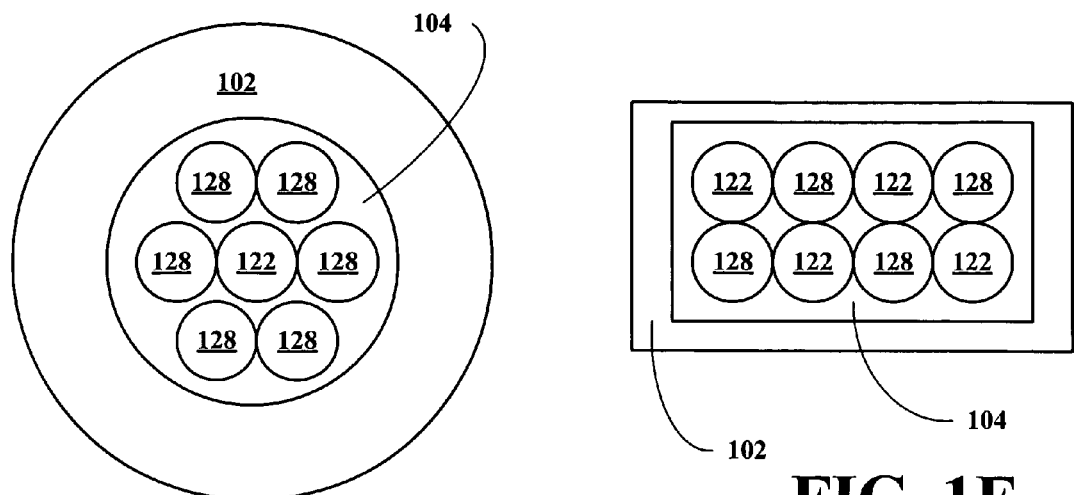
FIG. 1D
FIG. 1F
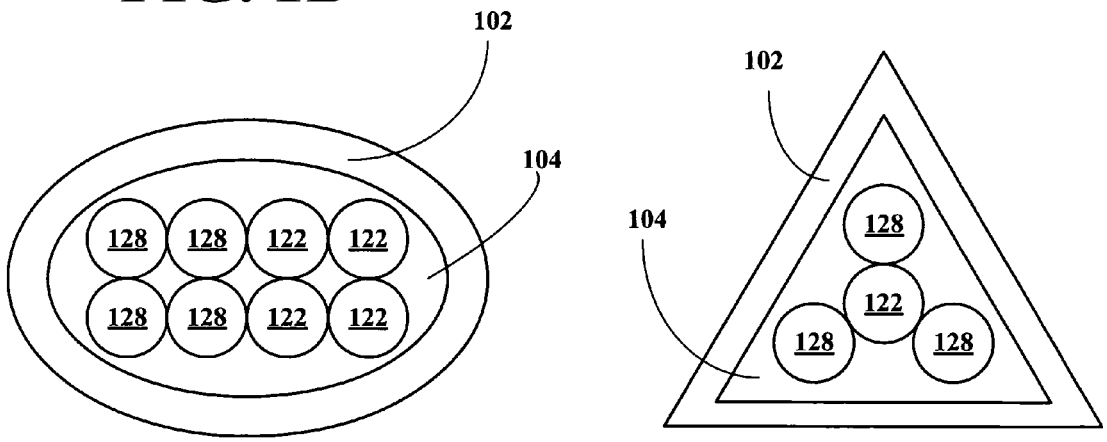
FIG. 1E
FIG. 1G

NONINVASIVE BLOOD ANALYSIS BY OPTICAL PROBING OF THE VEINS UNDER THE TONGUE

RELATED APPLICATIONS

This PCT Application, under United States law, claims provisional priority to U.S. Provisional Patent Application Ser. No. 60/465,134, filed 24 Apr. 2003.

BACKGROUND OF THE INVENTION

1. Field of the Invention

The present invention relates to a novel system and method for non-invasive analysis of blood including blood components and analytes.

More particularly, the present invention relates to a novel system and method for non-invasive analysis of blood including blood components and analytes, where the system is portable and pocket-sized and includes a probe having a tip designed to be placed in proximity to or in direct contact with tissue over a big vein on the underside of a patient's tongue, where the tip includes an excitation port through which an input signal generated by a signal generator subsystem impinges on a surface of tissue over the vein and a response port through which a response signal is received by and forwarded to a detector and analyzer or a detector/analyzer, which converts the response signal into a concentration of a blood component and/or a value of a blood parameter.

2. Description of the Related Art

Analysis of blood is needed for diagnostic and management of various diseases and conditions as well as for screening of healthy population. Current techniques and systems for blood analysis are invasive, require blood sampling, and cannot be performed in real time or continuously. At present, blood is usually analyzed in clinical laboratories after taking blood samples with invasive techniques.

Thus, there is a need in the art for a technique and system for noninvasive analysis of blood that would benefit a large population of patients and healthy people as well.

SUMMARY OF THE INVENTION

The present invention provides a system for non-invasive analysis of blood, including a probe having a tip designed to be placed in proximity to or in direct contact with tissue over a big vein on the underside of a patient's tongue, where the tip includes an excitation port through which an input signal generated by a signal generator subsystem impinges on a surface of the tissue over the vein and a response port through which a response signal is received by and forwarded to a detector and analyzer or a detector/analyzer, which converts the response signal into concentration of a blood component and/or a value of a blood parameter.

The present invention also provides a portable and pocket-sized system for non-invasive analysis of blood, including a probe having a tip designed to be placed in proximity to or in direct contact with tissue over a big vein on the underside of a patient's tongue, where the tip includes an excitation port through which an input signal generated by a signal generator subsystem impinges on a surface tissue over the vein and a response port through which a response signal is received by and forwarded to a detector and analyzer or a detector/analyzer, which converts the response signal into concentration of a blood component and/or a value of a blood parameter.

The present invention also provides a portable and pocket-sized system for non-invasive analysis of blood including an under the tongue apparatus comprising two side portions adapted to fit over teeth on each side of the lower jaw, a depressed portion between the two side portions including an excitation port through which an input signal generated by a signal generator subsystem impinges on a surface tissue over the vein and a response port through which a response signal is received by and forwarded to a detector and analyzer or a detector/analyzer, which converts the response signal into a concentration of a blood component and/or a value of a blood parameter.

The present invention also provides a system, including an excitation signal generator, a probe including a tip designed to be placed in proximity to or in contact with tissue over a big vein on the underside of a patient's tongue and having an excitation signal port connected to the generator via a signal transmission conduit and a response port connected to a detector which is in turn connected to an analyzer or a detector analyzer, where the analyzer converts the response signal into a concentration of a blood component and/or a value of a blood parameter.

The present invention also provides a portable and pocket-sized system for non-invasive glucose and/or cholesterol measuring and monitoring including a probe having a tip designed to be placed in proximity to or in direct contact with tissue over a big vein on the underside of a patient's tongue, where the tip includes an excitation port through which an input signal generated by a signal generator subsystem impinges on a tissue surface over the vein and a response port through which a response signal is received by and forwarded to a detector and analyzer or a detector/analyzer, which converts the response signal into concentrations of glucose and/or cholesterol in the blood.

The present invention also provides a portable and pocket-sized system for non-invasive hemoglobin, hematocrit, oxy-hemoglobin, deoxy-hemoglobin, carboxyhemoglobin, and/or glycosylated or glycated hemoglobin measuring and monitoring including a probe having a tip designed to be placed in proximity to or in direct contact with tissue over a big vein on the underside of a patient's tongue, where the tip includes an excitation port through which an input signal generated by a signal generator subsystem impinges on a tissue surface of the vein and a response port through which a response signal is received by and forwarded to a detector and analyzer or a detector/analyzer, which converts the response signal into concentrations of hemoglobin, hematocrit, oxy-hemoglobin, deoxy-hemoglobin, carboxyhemoglobin, and/or glycosylated or glycated hemoglobin in the blood.

The present invention provides a method for measuring and/or monitoring blood components and/or parameters including the steps of placing a tip of a probe having an excitation port and a response port in proximity to or in direct contact with tissue over a big vein on the underside of a patient's tongue. Once the tip is in proximity to or in contact with the tissue over the vein, an excitation signal is transmitted into the vein through the excitation port, where the excitation signal is generated by a signal generator connected to the excitation port of the probe via a signal transmission conduit. After the excitation signal or input signal is transmitted into the vein, the response port receives a response signal and detects the response signal in a detector.

The present invention provides a method for measuring and/or monitoring blood components and/or parameters including the steps of placing a tip of a probe having an excitation port and a response port in proximity to or in direct contact with tissue over a big vein on the underside of a patient's tongue. Once the tip is in proximity to or in contact with the tissue over the vein, an excitation signal is transmitted into the vein through the excitation port, where the excitation signal is generated by a signal generator connected to the excitation port of the probe via a signal transmission conduit. After the excitation signal or input signal is transmitted into the vein, the response port receives a response signal directly through a detector that generates a detector signal which is transmitted via a detector signal conduit to an analyzer or via a response signal conduit to a detector/analyzer. Once the signal has been detected, the analyzer converts the detected signal into a concentration of a blood component and/or a value of a blood parameter.

DESCRIPTION OF THE DRAWINGS

The invention can be better understood with reference to the following detailed description together with the appended illustrative drawings in which like elements are numbered the same:

FIGS. 1D-G depict three preferred embodiments of probes of this invention;

DETAILED DESCRIPTION OF THE INVENTION

Figure 1A:
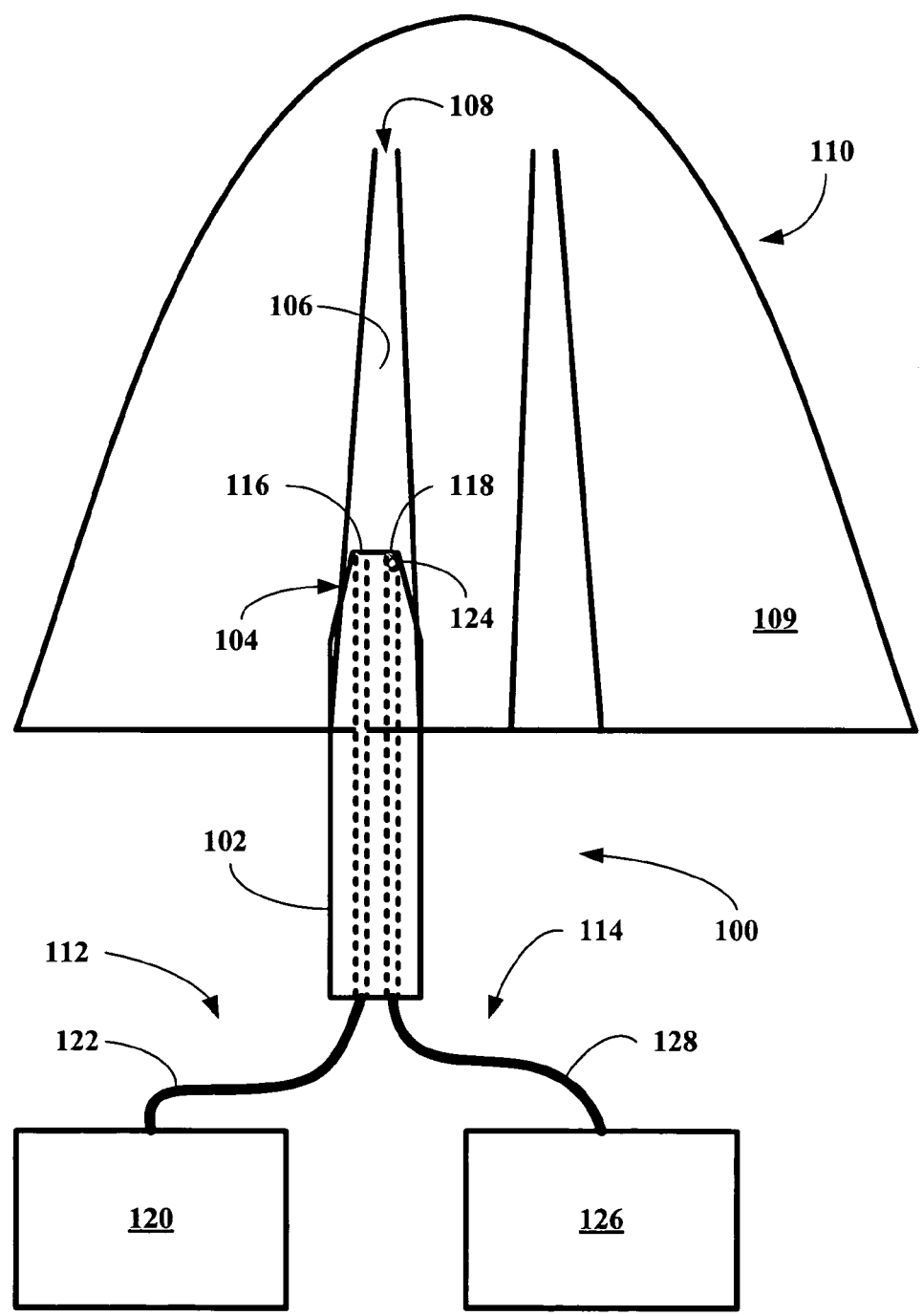
FIGS. 1A-C depict three preferred embodiments of apparatuses of this invention.

The inventor has found that a novel system and method for non-invasive analysis of blood including blood components and analytes can be constructed and used. Portable, pocket-sized devices can be developed for home and clinical use based on this technique permitting wide application for the apparatuses of this invention.

The technique is based on optical analysis of blood circulating in a big vein under a patient's tongue. Light from an optical probe of an apparatus of this invention is directed into one of these veins by bringing a probe tip in close proximity to or in contact with the surface of tongue tissue above the vein, i.e., the tip of the probe is brought into proximity to or in contact with epithelial tissue overlying the big veins beneath the surface of the underside of the tongue. Non-contact analysis may ultimately be the preferred method from a medical and practical point of view because the tip does not make contact with the tissue, thereby reducing the possibility of infections. The emitted light interacts with blood flowing through the vein, producing a signal. The produced or output signal is received or received and measured by the probe, where the output signal will depend on optical properties of the blood. The optical properties of the blood are related to concentrations of blood components. Because the tissues between the probe tip and blood circulating in the vein is very thin, the output signals received by the apparatuses of this invention have minimal influences from the intervening tissue (i.e., minimal background signals) caused by light scattering and absorption in the intervening tissue.

The term "in proximity to" means that the probe tip is sufficiently close to the surface tissue of the underside of the tongue of a patient to produce a response signal of sufficient intensity to be measured. Generally, the distance is between about 10 mm and about 1 mm, with distances between about 5 mm and 1 mm being preferred. However, larger or smaller distances can be used as well provided an analyzable signal can be detected. The term "in contact with" means that the probe tip actually makes physical contact with the tissue of the underside of the patient's tongue.

The excitation light can be in the near infrared (wavelength range from about 760 to about 2,500 nm), the visible (wavelength range from about 400 to about 760 nm), or the near UV (from about 250 to about 400 nm) portions of the electromagnetic spectrum. These portions of the electromagnetic spectrum would have insignificant background signals due to relatively low scattering and absorption in the intervening tissue compared with light from other spectral ranges.

The method and system of this invention can utilize any optical detection technique or hybrid detection techniques including, but not limited to, reflectance techniques, confocal techniques, scanning confocal techniques, polarization techniques, interferometry techniques, optoacoustic techniques, low coherence reflectometry techniques, techniques based on speckle measurements, or similar techniques or mixtures or combinations thereof.

One preferred application of this invention is noninvasive measurement of hemoglobin concentration and/or hematocrit in blood. Other applications of the systems and methods of this invention include, without limitation, noninvasive measurements of glucose and/or cholesterol concentrations in blood and potentially can be used for measuring oxy-, deoxy-, carboxyhemoglobin, and/or glycosylated hemoglobin concentrations in blood. Other applications include, without limitation, measuring or monitoring analytes, drugs, exogenous substances, and/or blood parameters (such as pH).

This technique can be used for blood analysis of healthy population and patients with various diseases and disorders including critically ill patients.

Figure 1B:
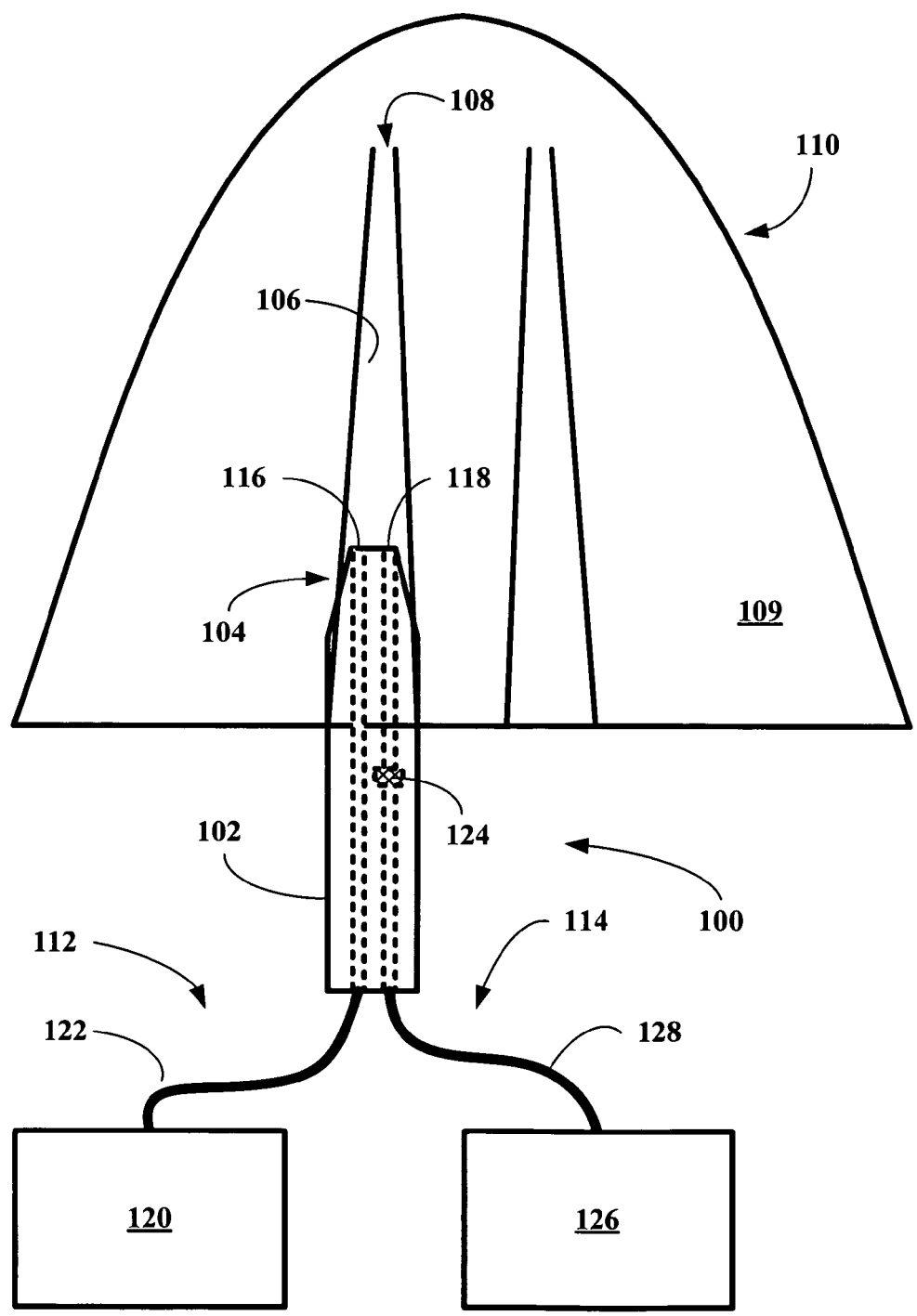
Figure 1C:
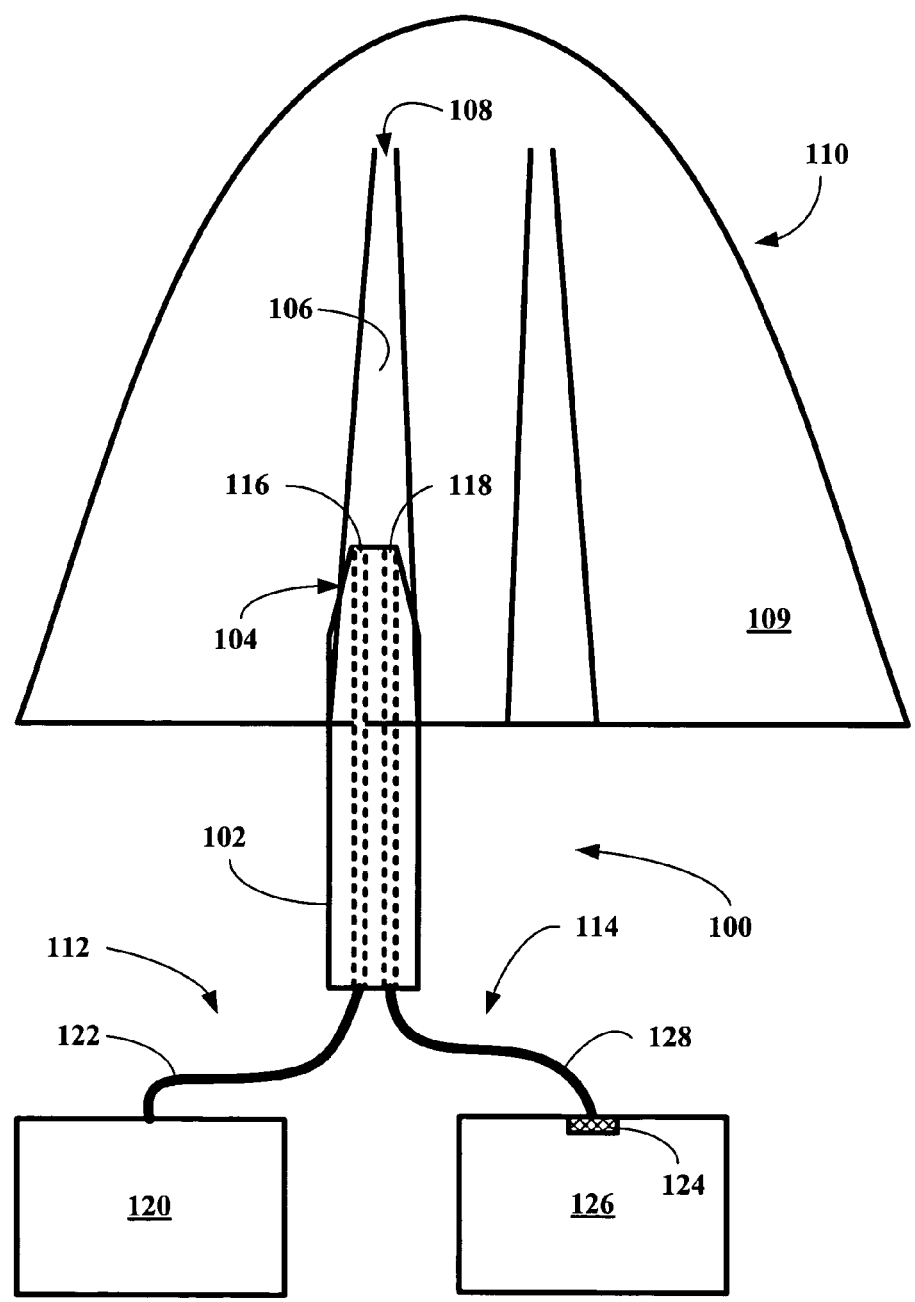

Referring now to FIGS. 1A-D, a preferred embodiment of a system of this invention, generally 100, is shown to include a probe 102 having a tip 104, which is in proximity to or in contact with a surface tissue 106 over a vein 108 of an underside 109 of a patient's tongue 110. The system 100 also includes a light delivery subsystem 112 and detection/analysis subsystem 114. The light delivery subsystem 112 terminates in the probe tip 104 at a light outlet or port 116, while the detection/analysis subsystem 114 begins in the tip 104 at an output or response signal inlet or port 118. The light delivery subsystem 112 includes a light source 120 and a light conduit 122 terminating at the light outlet 116. Preferably, the light conduit 122 is an optical fiber or optical fiber bundle and the light source 120 is a laser or filtered broad spectrum light source (e.g., lamp). The detection/analysis subsystem 114 includes a detector 124, an analyzer unit 126 and a signal conduit 128 interconnecting the detector 124 and the analyzer 126. The detector 124 can be located in the tip 104 as shown in FIG. 1A, in the probe 102 as shown in FIG. 1B or in the analyzer unit 126 as shown in FIG. 1C. The output signal forwarded to the analyzer 126 can be optical and/or acoustic, if the detector 124 is located in the analyzer 126 or electrical, if the detector 124 is located in the probe 104.

Referring now to FIGS. 1D-G, several probe tip and optical fiber arrangements are shown. Looking at FIG. 1D, the light conduit 122 is a single optical fiber, while the signal conduit 128 includes six optical fibers surrounding the light conduit 122 for a cylindrical probe 102 and circular probe tip 104. Looking at FIG. 1E, the light conduit 122 includes four fibers and the signal conduit 128 includes four optical fibers surrounding the light conduit 122 arranged side by side for an oval shaped probe 102 and tip 104. Looking at FIG. 1F, the light conduit 122 includes four fibers and the signal conduit 128 includes four optical fibers surrounding the light conduit 122 arranged intermixed for a rectangular probe 102 and probe tip 104. Looking at FIG. 1G, the light conduit 122 includes one fiber and the signal conduit 128 includes three optical fibers surrounding the light conduit 122 for a triangular probe 102 and probe tip 104.

Figure 1H:
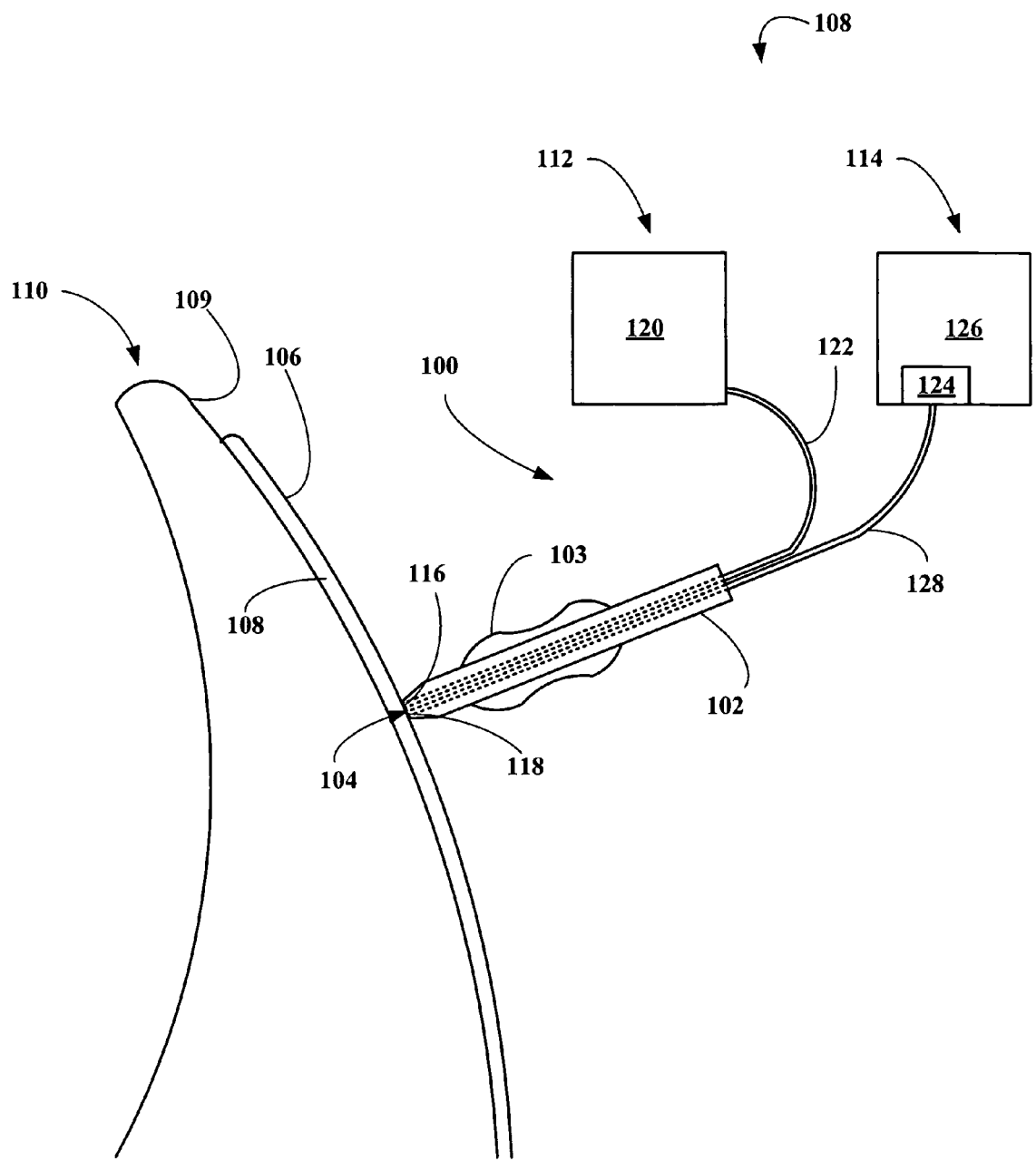
FIG. 1H depict another embodiments of apparatus of this invention.

Looking at FIG. 1H, the system 100 works by placing the probe tip 104 in contact with the surface tissue 106 over the vein 108. In this figure, the probe 102 also includes a finger grip 103 for better control of the probe tip placement. The light delivery system 112 is then activated, turned on, and excitation radiation travels from the light source 120 through the light conduit 122 and out the light outlet 116 in the probe tip 104. The excitation radiation then propagates through the surface tissue 106, a relatively thin tissue layer, and into the vein 108 where a response signal is produced. The response signal then enters the signal port 118 where it is either detected by the detector 124 in the probe 102 or the probe tip 104 or travels down the signal conduit 128 to the detector 124 associated with the analyzer unit 126. The detector 124 converts the signal into a detector response and the analyzer converts the response into a concentration of a blood component and/or a value of a blood parameter.

Figure 2A:
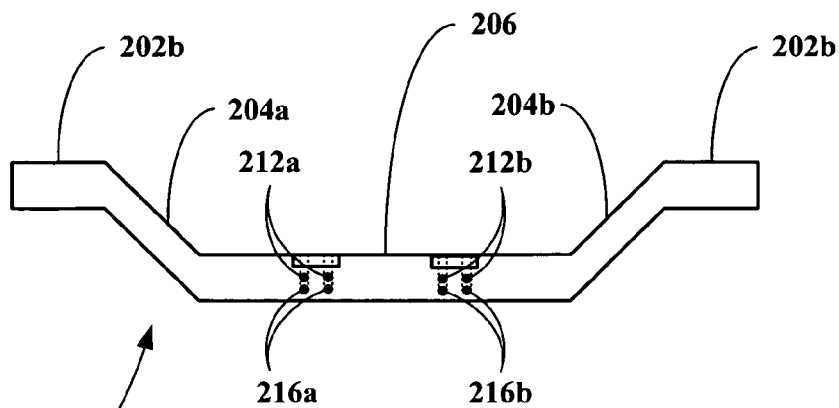
FIG. 2 depicts another preferred embodiment of an apparatus of this invention, designed like an under tongue retainer.
Figure 2B:
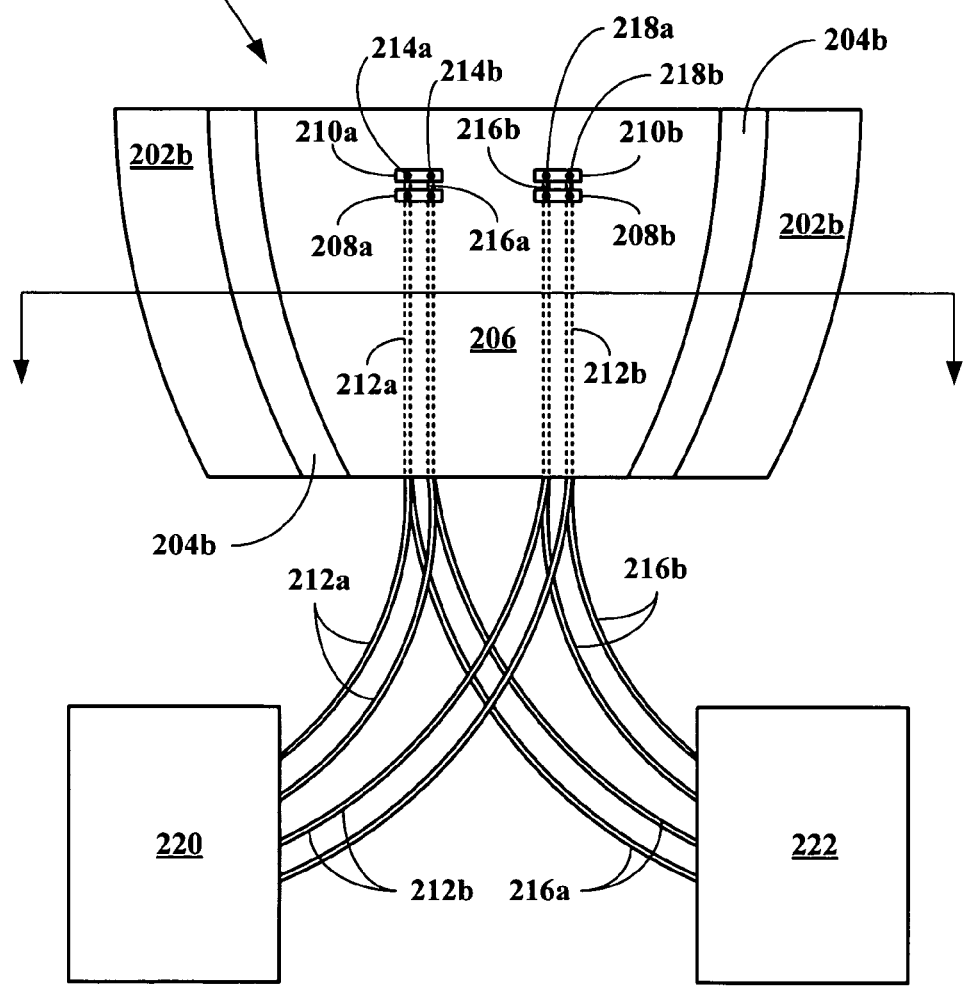

Referring now to FIG. 2, a second embodiment of an apparatus of this invention, generally 200, is shown to include a first teeth engaging side section 202a, a second teeth engaging side section 202b, a first and a second downwardly extending sections 204a&b and a middle section 206 bridging the two downwardly extending sections 204a&b adapted to contact the underside of a patient's tongue (not shown). The middle section 206 includes two emitters 208a&b and two receivers 210a&b. Extending from the two emitters 208a&b and the two detectors 210a&b are light conduits 212a&b, shown here as two optical fibers 214a&b terminating at the emitters 208a&b, and signal conduits (light or sound) 216a&b, also shown here as to optical fibers 218a&b terminating at the receivers. The light conduits 212a&b are connected to a light source 220, while the signal conduits 216a&b are connected to a detector/analyzer 222.

THEORETICAL SECTION OF THE INVENTION

Most tissues are strongly scattering media in the visible and near-IR spectral range. Three major optical parameters are responsible for distribution of light in tissues: 1) the absorption coefficient ($\mu_a$); 2) the scattering coefficient ($\mu_s$); and 3) the effective attenuation ($\mu_{eff}$) coefficient. The effective attenuation coefficient ($\mu_{eff}$) is related to $\mu_a$, $\mu_s$, and the anisotropy factor (g) thusly:

(1)

where $\mu_s(1-g)$ is the reduced scattering coefficient, $\mu_s'$[1]. Light penetration depth in tissues is defined as $1/\mu_{eff}$. Absorption and reduced scattering coefficients of tissues are moderate in the visible spectral range and low in the near-IR spectral range (from 600 to 1600 nm), which results in deeper penetration of visible and especially near-IR radiation compared with that of other parts of the spectrum. Application of visible or near-IR radiation will allow insignificant attenuation of light in the thin tissues between the vein on the underside of the tongue and the probe.

Hemoglobin has a high absorption coefficient in the visible and near-IR spectral range that is dependent on hemoglobin oxygen saturation (the ratio of oxyhemoglobin to total hemoglobin (THb) [1]. The blood absorption coefficient, $\mu_a$ [blood], is related to oxyhemoglobin concentration (C[oxy]) and deoxyhemoglobin concentration (C[deoxy]) as follows:

$$\mu a \text{ [blood]} = C[\text{oxy}] \times K[\text{oxy}] + C[\text{deoxy}] \times K[\text{deoxy}] \qquad (2)$$

where K[oxy] and K[deoxy] are known values of extinction coefficients of oxy-and deoxyhemoglobin at a given wavelength. Since K[oxy]=K[deoxy]=K at isosbestic wavelengths and THb=C[oxy]+C[deoxy], one can measure hemoglobin in the veins because:

$$\mu a[\text{blood}] = THb \times K \qquad (3)$$

The tissue between the vein on the underside of the tongue and the probe is optically thin in the visible and near IR spectral ranges because: $\mu_{eff} \times L << 1$ due to relatively low $\mu_{eff}$ (~1-5 cm$^{-1}$) and small L (~0.01-0.02 cm). In contrast, blood in the vein is optically thick: $\mu_{eff,blood} \times L_{blood} >> 1$ because $\mu_{eff,blood}$ is high (~10 cm$^{-1}$) and L is about 2 to 3 mm. Attenuation is the tissue is insignificant and all signal will be from blood. The signal from the deeper tissues will not be significant due to strong light attenuation by blood in the vein.

EXPERIMENTAL DATA OF THIS INVENTION

Figure 3:
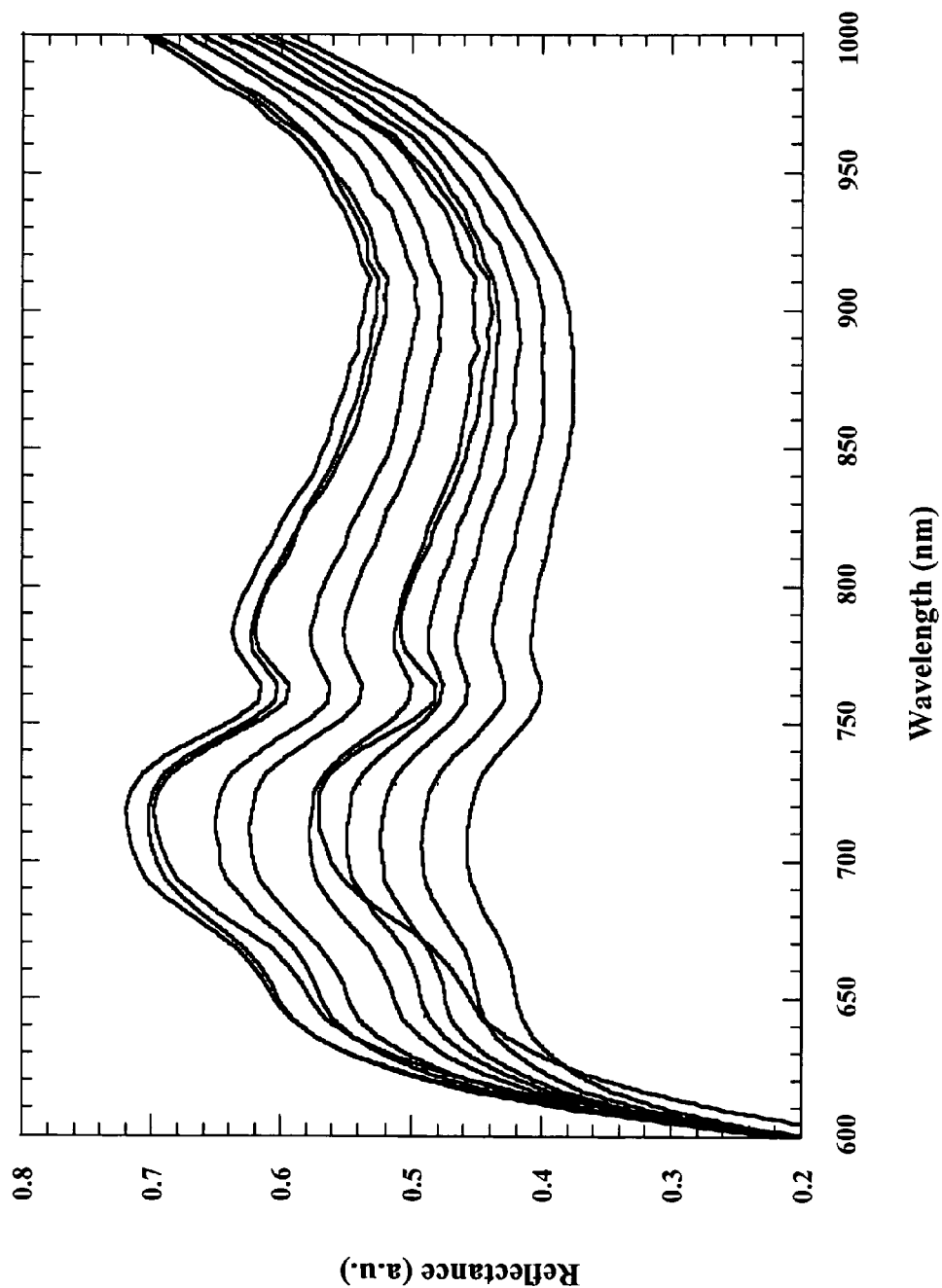
FIG. 3 depicts a reflectance spectra measured from sheep blood at different THb.

FIG. 3 shows diffuse reflectance spectra obtained from sheep blood at different total hemoglobin concentration (THb) through the cylindrical wall (thickness 0.8 mm) of a 10-mL syringe. Blood with an initial THb of 8.2 g/dL, oxygenation of 56%, and volume of 5 mL was progressively diluted with saline with increments of 0.5 mL. The final concentration was 4.1 g/dL. The spectra were obtained with a portable (pocket size) spectrometer (range from 600 to 1180 nm) operated with a laptop computer. This range included the isobestic wavelength of 805 nm, where oxy-and deoxyhemoglobin have the same absorption coefficient. Therefore, variations of blood oxygenation do not influence the accuracy of THb measurement at this wavelength. The sample was irradiated by a tungsten lamp (the lamp and its power supply are compact: pocket size; designed for this spectrometer) through a reflection probe combining one 0.4-mm illumination fiber and six 0.4-mm fibers around it for detection of the reflectance signal. The system was calibrated with a reflectance standard with 25% reflectivity. The standard is being widely used for calibration of optical spectroscopic instruments in a wide spectral range that includes ultraviolet (UV), visible, and near infra-red (near-IR) spectral ranges.

The diffuse reflectance signal is due to light scattering from red blood cells in blood. All spectra had: (1) a minimum at 760 nm due to the absorption peak (maximum of absorption) at this wavelength for deoxygenated hemoglobin and (2) low intensity at 600 nm due to strong absorption by hemoglobin. The spectra were dependent on THb. In this geometry of irradiation, the reflectance signal first increased and then decreased with dilution.

Figure 4:
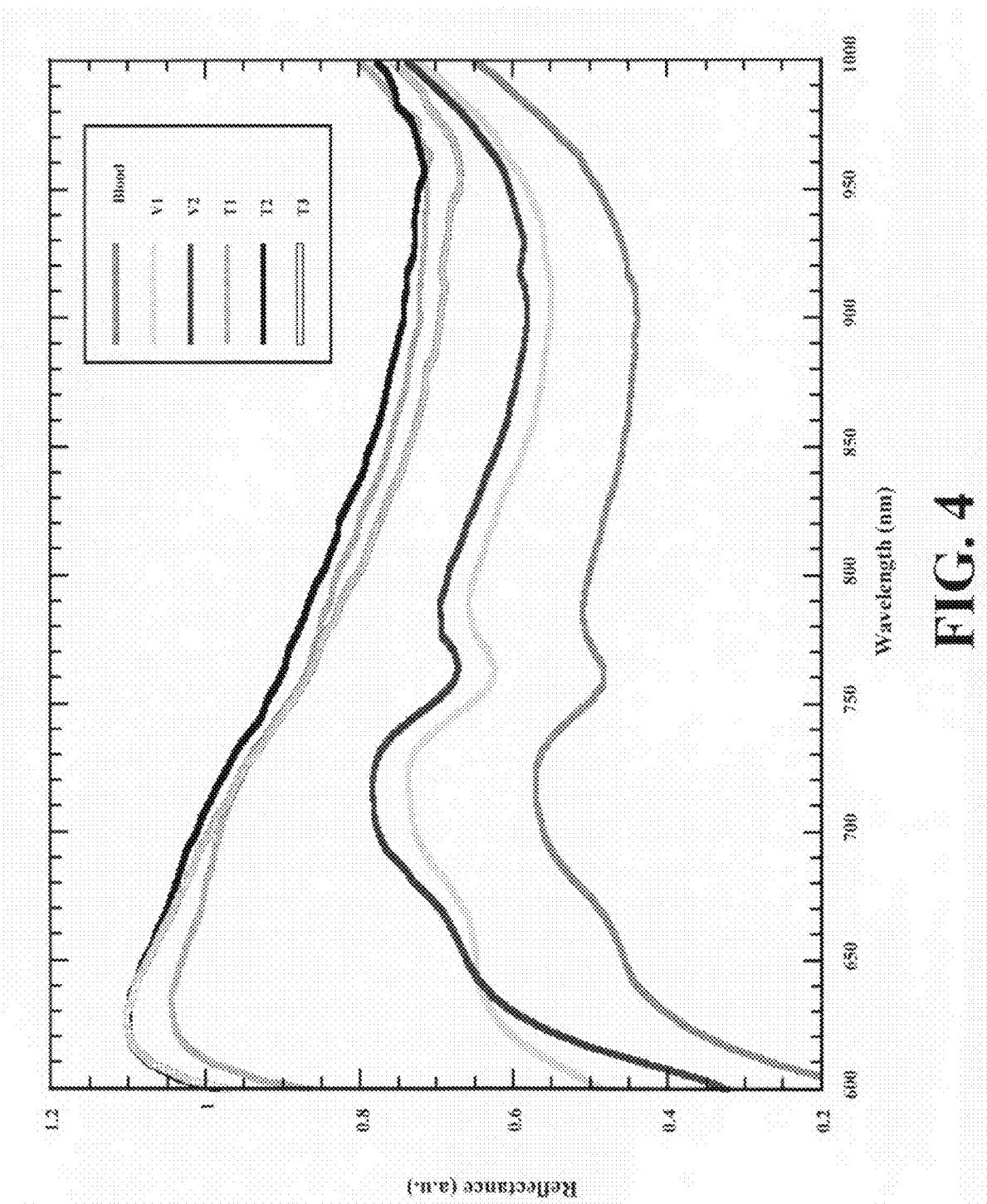
FIG. 4 depicts a reflectance spectra measured from blood in vitro, the two veins (V1 and V2), and tongue tissue (T1, T2, and T3) on the underside of the tongue.

Since the tissues between the blood circulating in the tongue vein and the probe are very thin (01.-0.2 mm), they are optically thin in the visible and near-IR spectral ranges due to low tissue absorption. Therefore, the reflectance signal from blood circulating in the vein is not influenced by variation of optical properties of the tissue. FIG. 4 shows representative reflectance spectra measured: (1) in vitro from blood; (2) in vivo from the two big veins (V1 and V2) on underside of the tongue of a healthy volunteer; and (3) at three locations: right, left and middle part of the underside of the tongue (T1, T2, and T3, respectively). It is clearly seen that the spectra measured from the veins are similar to that of blood. As in pure blood, the spectra have minimum values at 760 nm and low intensity at 600 nm. The spectra measured from the tongue tissue are different from that of pure blood: high intensity at 600 nm and no minimum at 760 nm.

The reflectance signal at a given THb and oxygenation is dependent on wavelength and the reflectance probe configuration. We performed experiments with different probes in a wide spectral range with two spectrometers operating in the range from 520 to 1180 nm and from 900 to 1700 nm.

Figure 5:
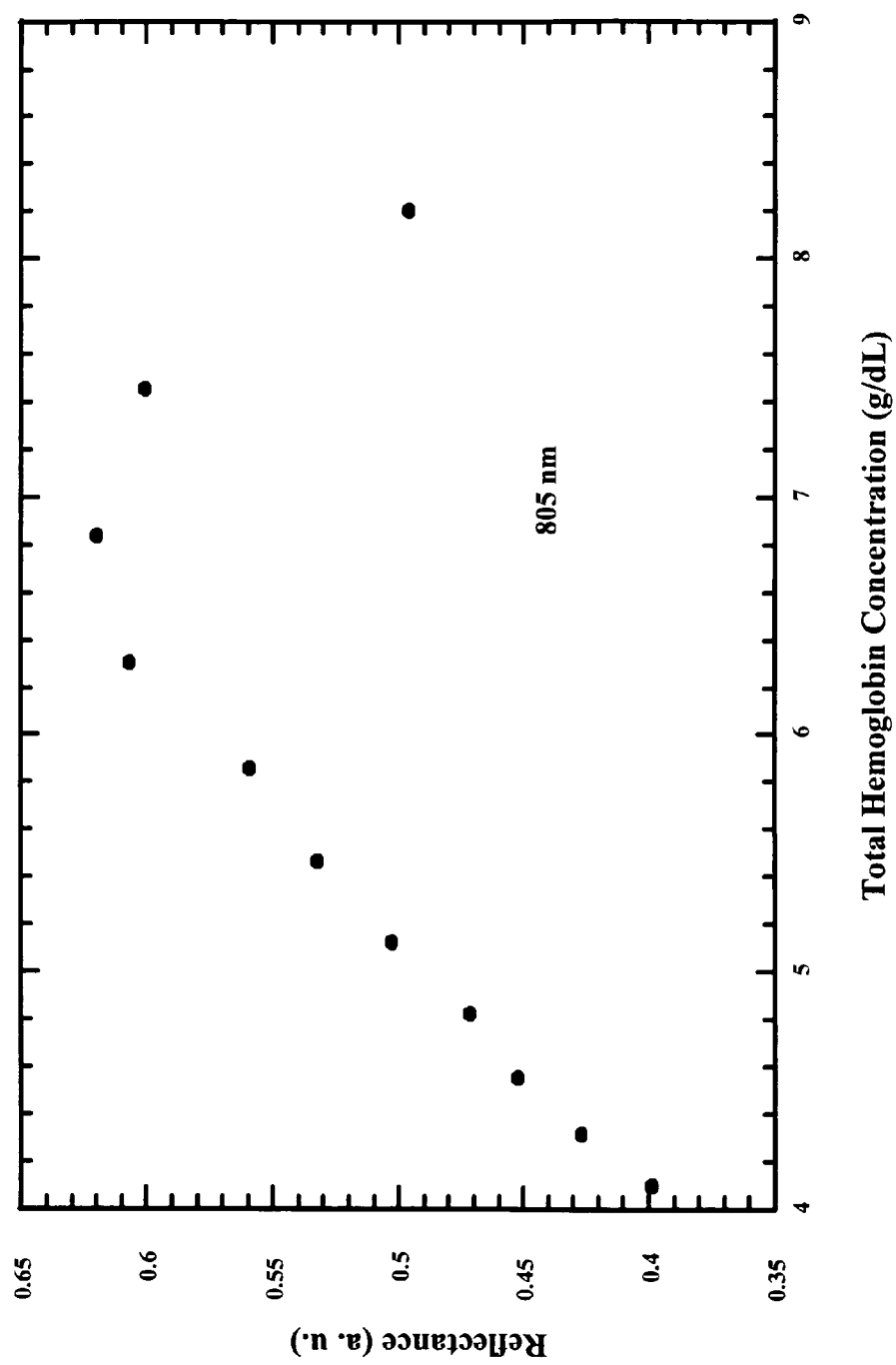
FIG. 5 depicts a reflectance signal from sheep blood vs. THb at 805 nm.

FIG. 5 shows the reflectance signal at 805 nm vs. THb for the spectra presented in FIG. 3. The signal is linearly dependent on THb from 4.1 to 6.3 g/dL.

Figure 6A:
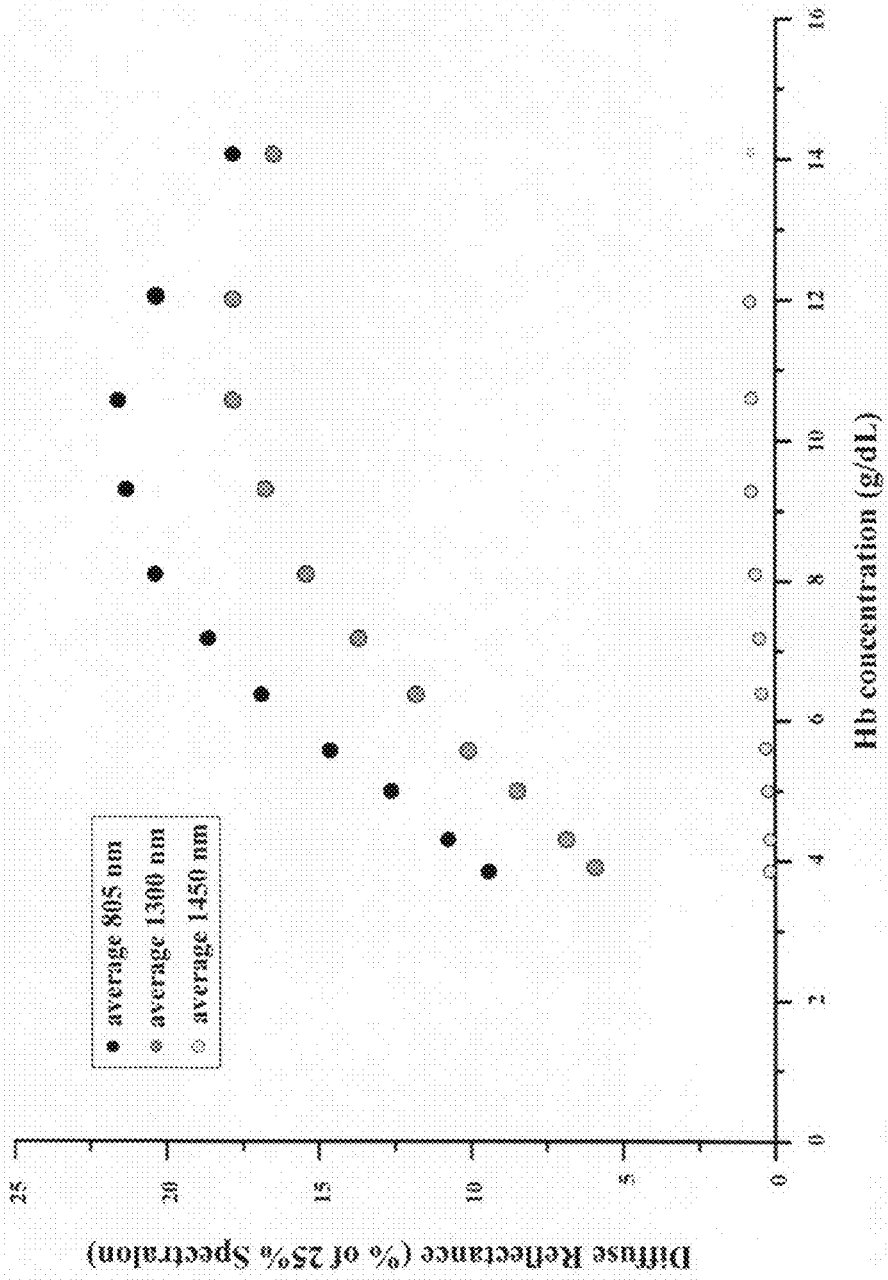
FIGS. 6A-B depict a reflectance signal from circulating sheep blood vs. THb at 805, 1300, and 1450 nm and measurements performed through 0.15-mm glass slide.
Figure 6B:
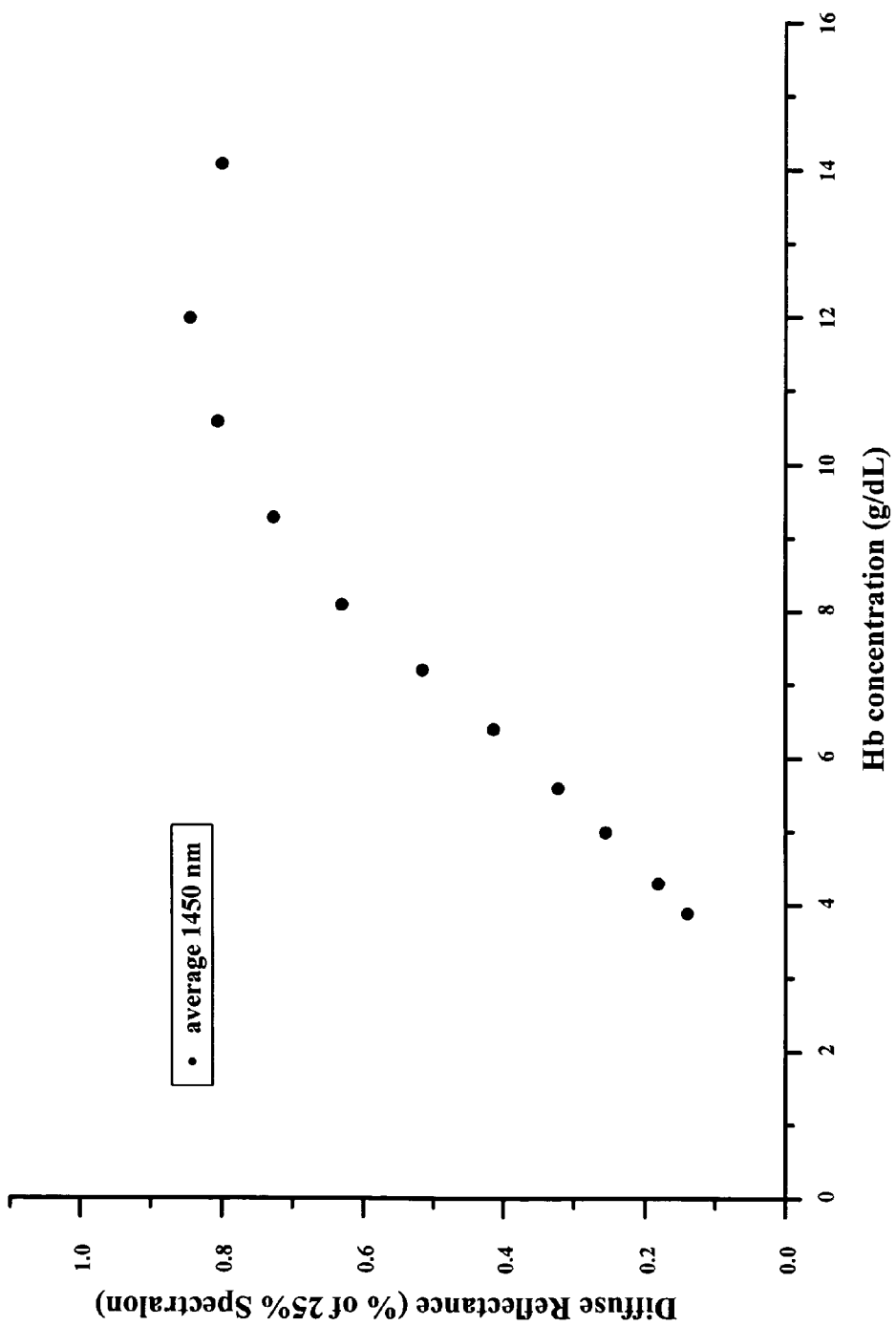
Figure 7A:
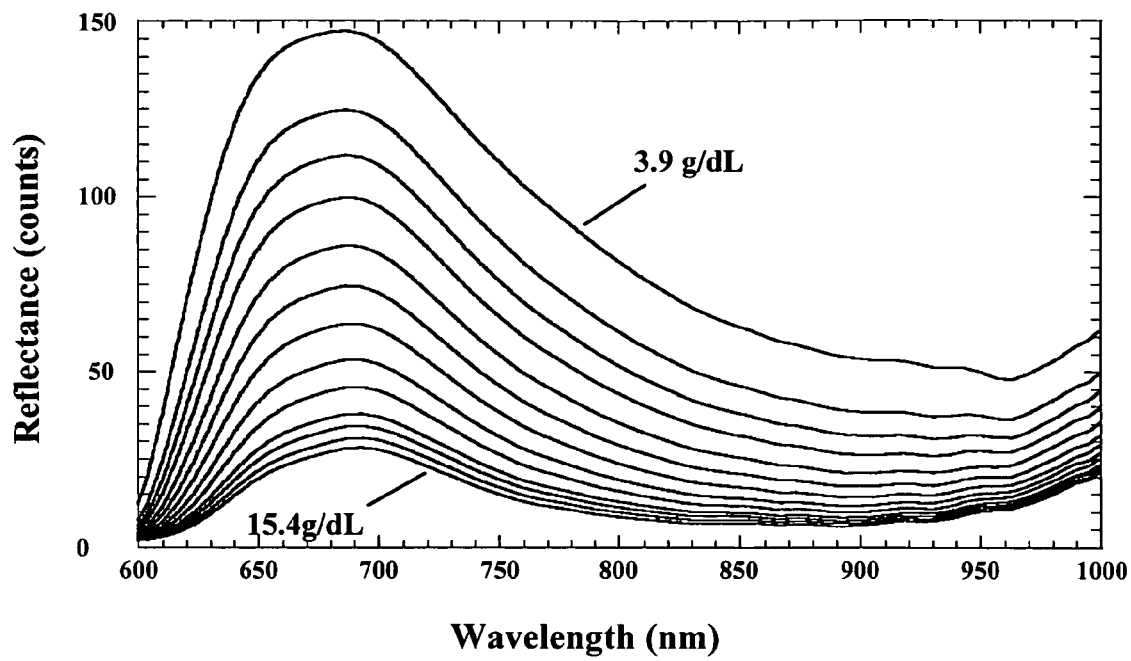
FIGS. 7A-B depict a reflectance spectra measured from sheep blood at different Thb and measurements performed by using a probe with 3-mm distance between irradiation and detection fibers through 0.15-mm glass slide.
Figure 7B:
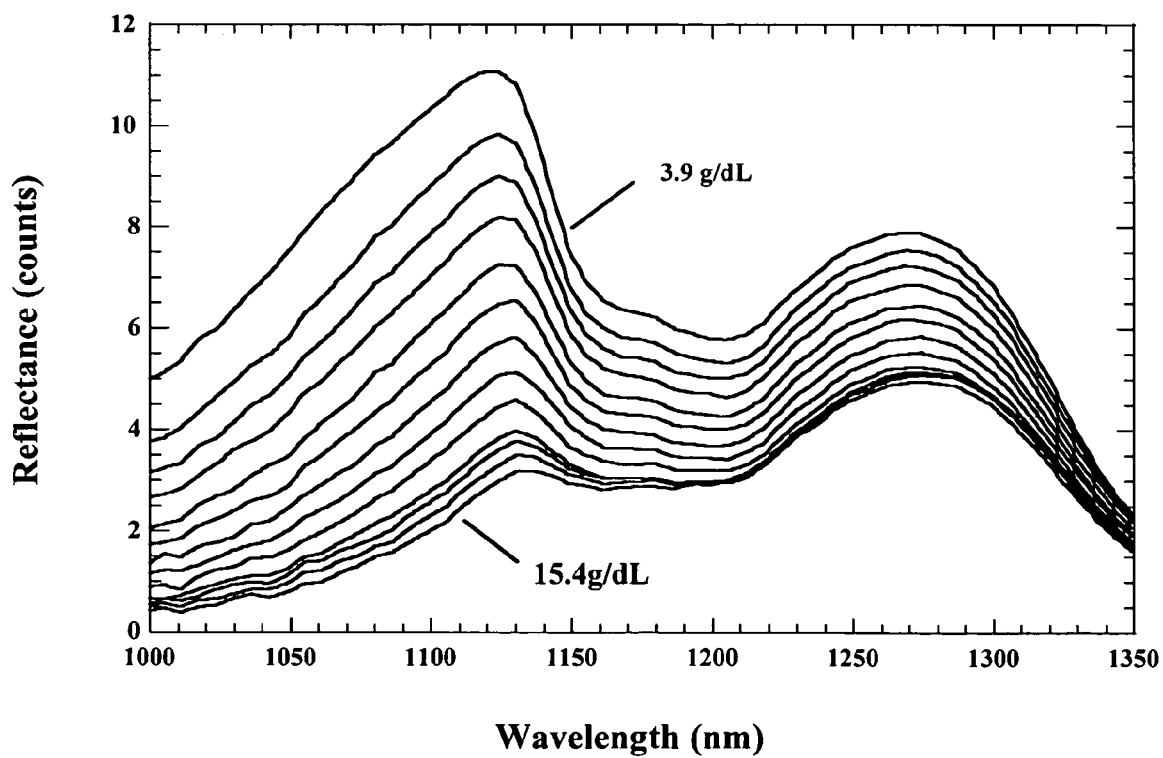

Another set of experiments was performed with circulating centrifuged sheep blood. Typically, THb of sheep blood (6-9 g/dL) is lower than that of human blood (11-16 g/dL). By using the centrifuge one can obtain blood with THb up to 14-16 g/dL (typical for human blood). To simulate the gap of 0.1-0.2 mm between the veins and the probe, we used a thin (0.15 mm) microscopic glass slide cover. FIGS. 6A and 6B show reflectance spectra obtained from blood (initial THb of 14.1 g/dL) with the two spectrometers, respectively. Both spectra were measured simultaneously by using a fiber-optic splitter attached to the detection fibers of the probe. One can see that the spectra are dependent on THb in both spectral ranges. Reflectance signals are presented as a function of THb for 805 and 1300 nm in FIG. 7A. The dependence was linear up to approximately 8 and 9 g/dL for the wavelengths of 805 and 1300 nm, respectively. At 1450 nm, it was linear up to 10 g/dL as shown in FIG. 7B.

Figure 8A:
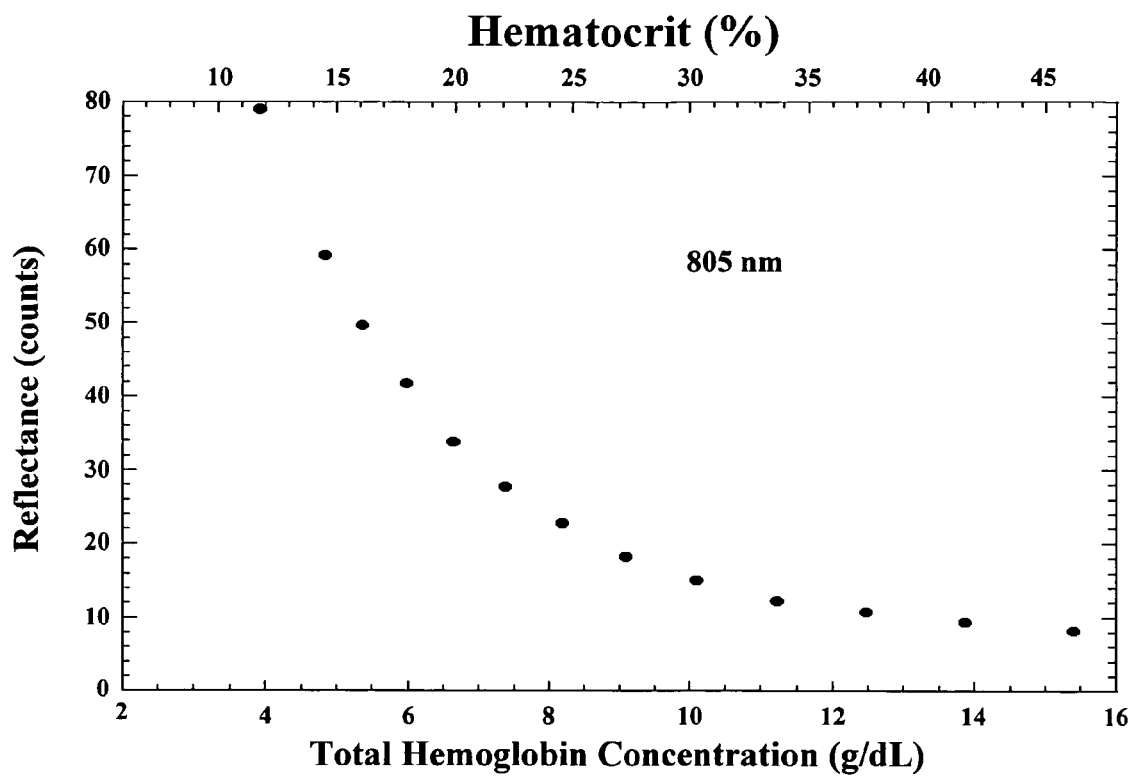
FIGS. 8A-B depict a reflectance signal from sheep blood vs. THb at 805 nm (a) and 1300 nm (b), where measurements were performed through 0.15-mm glass slide.
Figure 8B:
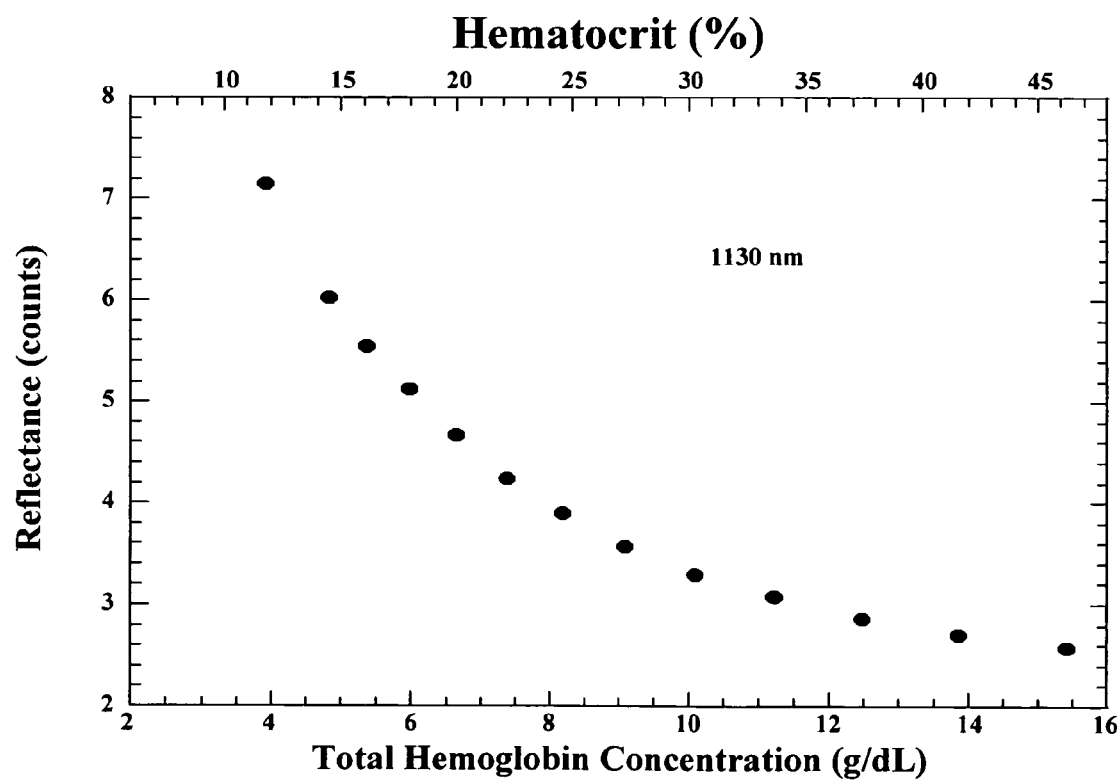

Blood dilution lowers both the absorption coefficient (which is proportional to THb up to 1150 nm) and the scattering coefficient (which is proportional to hematocrit). In general, total diffuse reflection (all photons that are reflected from tissue due to scattering) decreases with the absorption coefficient and increases with scattering coefficient and should be constant for tissues if both these coefficients decrease proportionally. However, spatial distribution of the diffusively reflected light varies with blood dilution. Therefore, the reflection signal from blood is strongly dependent on the distance between the irradiation and detection fiber. To accurately measure THb and hematocrit, one needs to find a configuration of the probe with optimal distance between the irradiation and detection fibers. We performed a set of experiments with a probe that has a 3-mm distance between irradiation and detection fibers. Gradual increase of the reflectance signal was obtained in a wide spectral range from 600 to 1180 nm as shown in FIGS. 7A&B with blood dilution. FIGS. 8A&B demonstrated the increase of the reflectance signal with dilution at 805 and 1130 nm, respectively. The increase of the reflectance signal with THb is due to deeper penetration of light in blood (decrease of blood effective attenuation coefficient). More photons can reach the detection fiber (separated by 3 mm from the irradiation fiber) at lower effective attenuation coefficient.

The obtained results demonstrate that one can measure THb and hematocrit with this technique if optimum probe configuration and wavelengths are used. A probe with detection fibers aligned on one or two opposite sides from the irradiation fiber (and along the vein) may provide very accurate measurement because the value of the signals measured at different distances from the irradiation fiber can be used in the calculation of THb and hematocrit.

Figure 9A:
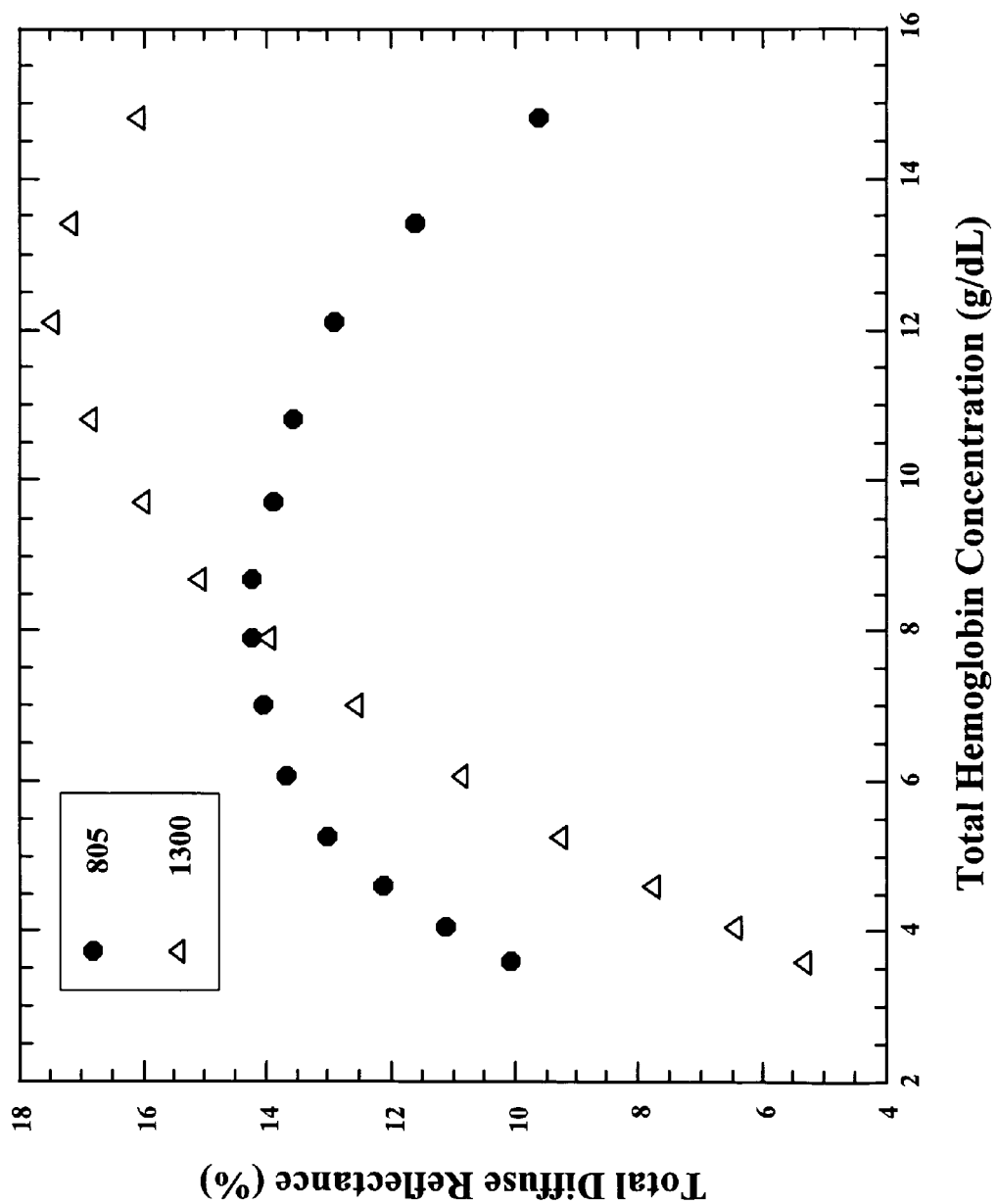
FIGS. 9A-B depict a total diffuse reflectance spectra ($R_d$) measured from sheep blood at different Thb, where measurements were performed by using an integrating sphere that collects all diffusively reflected light.
Figure 9B:
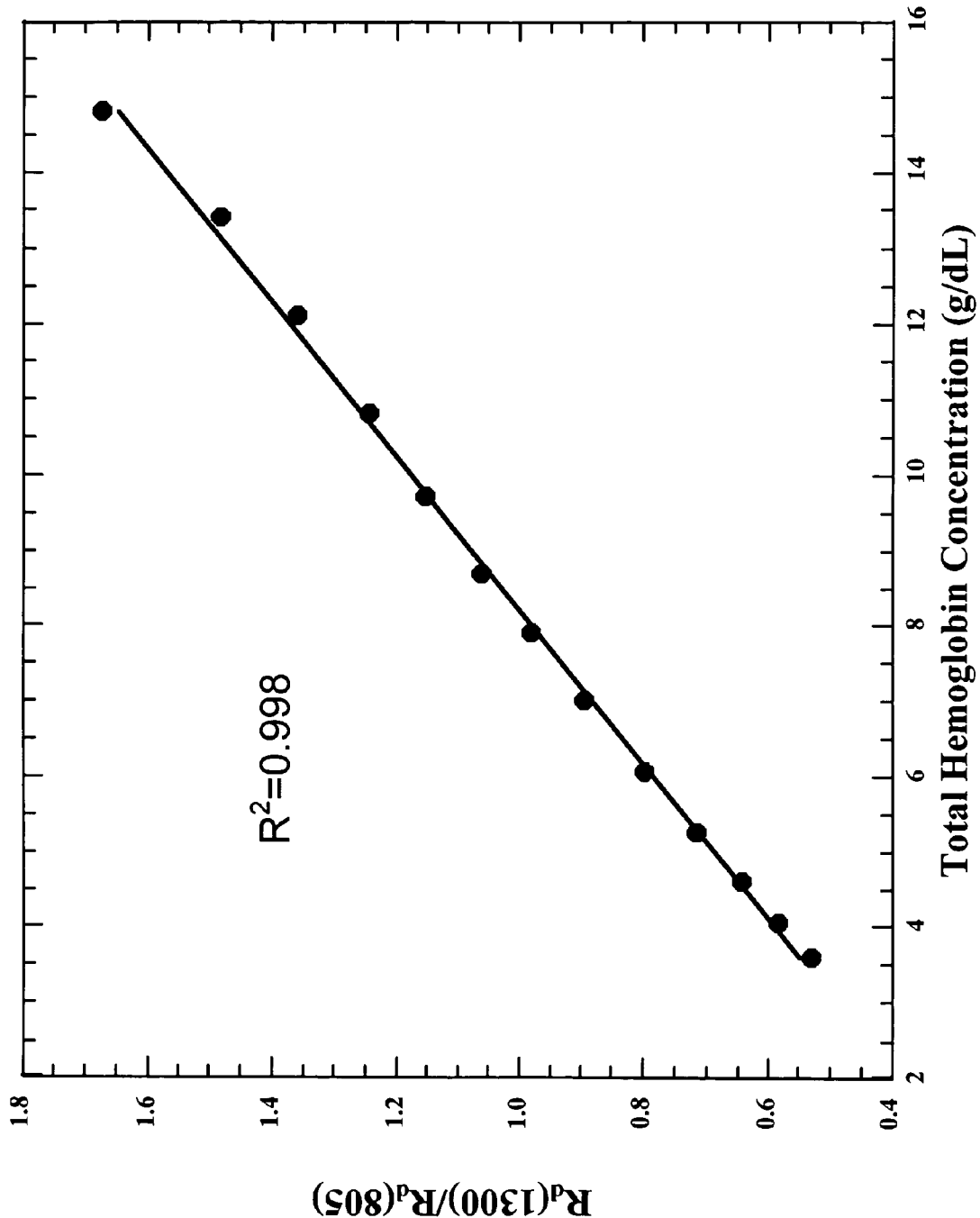

To find optimal wavelength we measured total diffuse reflectance $R_d$ of blood with an integrating sphere and both spectrometers. The studies with integrating spheres are being used for measurement of optical properties of absorbing and scattering media. Sheep blood was centrifuged and gradually diluted as described above. The integrating sphere allowed to detect all photons reflected back due scattering by blood cells. FIGS. 9A-B shows spectra obtained from sheep venous blood (initial THb=14.8 g/dL; oxygenation=57%; Hct=44.4%) at different THb concentrations. Decrease of THb resulted in different changes in different part of the spectra. One can see that the oxygenation gradually increased (the maximum at 760 nm is less pronounced at lower THb) due to penetration of oxygen in blood during dilutions. However, variations of the oxygenation in blood do not affect accuracy of measurements, if we use isosbestic wavelengths for analysis of the data and calibration of the system.

Figure 10A:
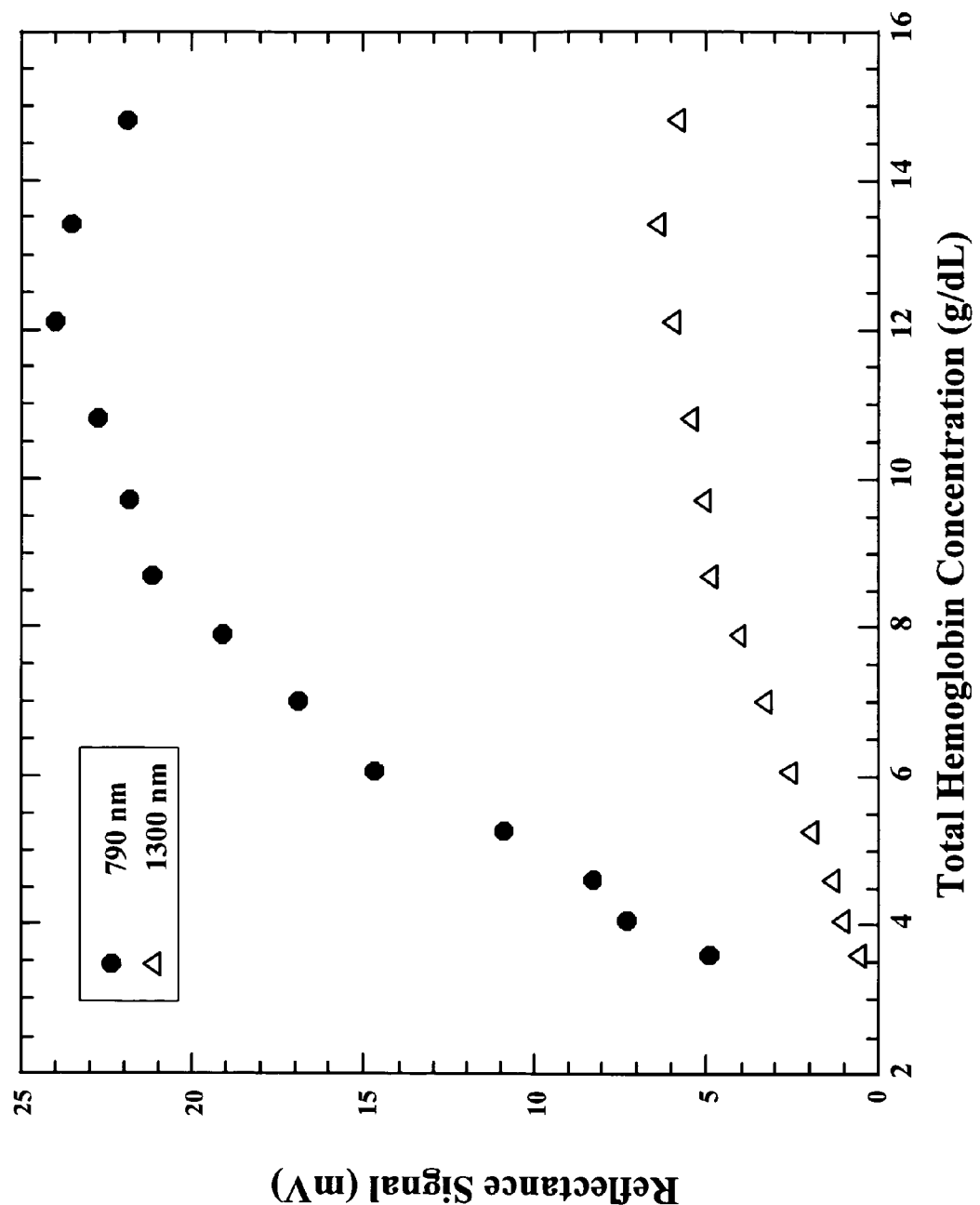
FIGS. 10A-B depict a total diffuse reflectance from sheep blood at 805 nm and 1300 nm (a) and the ratio $R_d(1300)/R_d(805)$ (b) vs. THb, where measurements were performed with the integrating sphere.
Figure 10B:
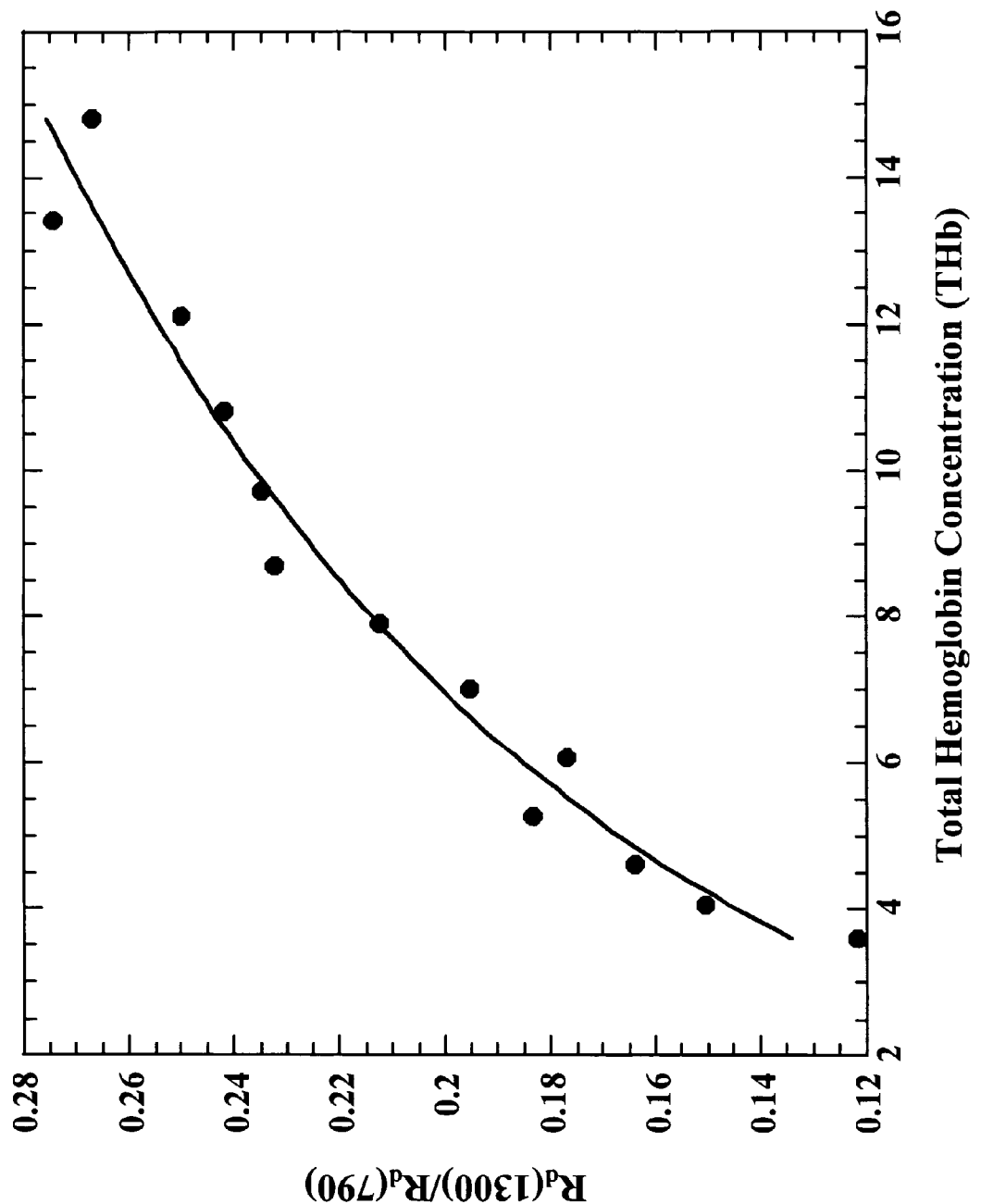

We plotted $R_d$ vs. THb at two isosbestic wavelengths: 805 and 1300 nm as shown in FIG. 10A. We also calculated the ratio $R_d(1300\text{ nm})/R_d(805\text{ nm})$ and obtained a linear dependence in the whole range of THb (from 3.6 to 14.8 g/dL) with the correlation coefficient of $R^2$=0.998 as shown in FIG. 10B. This demonstrates good correlation between the ratio $R_d(1300\text{ nm})/R_d(805\text{ nm})$ and THb and indicates that this ratio can be used for accurate measurement of THb. The linear dependence was obtained at these wavelength because: (1) $R_d \sim \mu_s'/\mu_a$ at relatively high $\mu_a$ typical of blood and (2) $\mu_a$ at 805 nm is linearly proportional to THb (negligible water absorption) and is constant at 1300 nm (negligible Hb absorption). This combination results in the linear dependence of $R_d(1300\text{ nm})/R_d(805\text{ nm})$ vs. THb.

One can use these two wavelengths and this algorithm to accurately measure THb. We designed, built, and tested a compact inexpensive laser diode based-system operation at two wavelengths: 1300 nm and 790 nm (which is close to 805 nm). Although the use of integrating spheres (irradiation and detection window of about 1 cm) is possible for the noninvasive blood analysis, it is easier and more practical to use probes with smaller size.

Figure 11A:
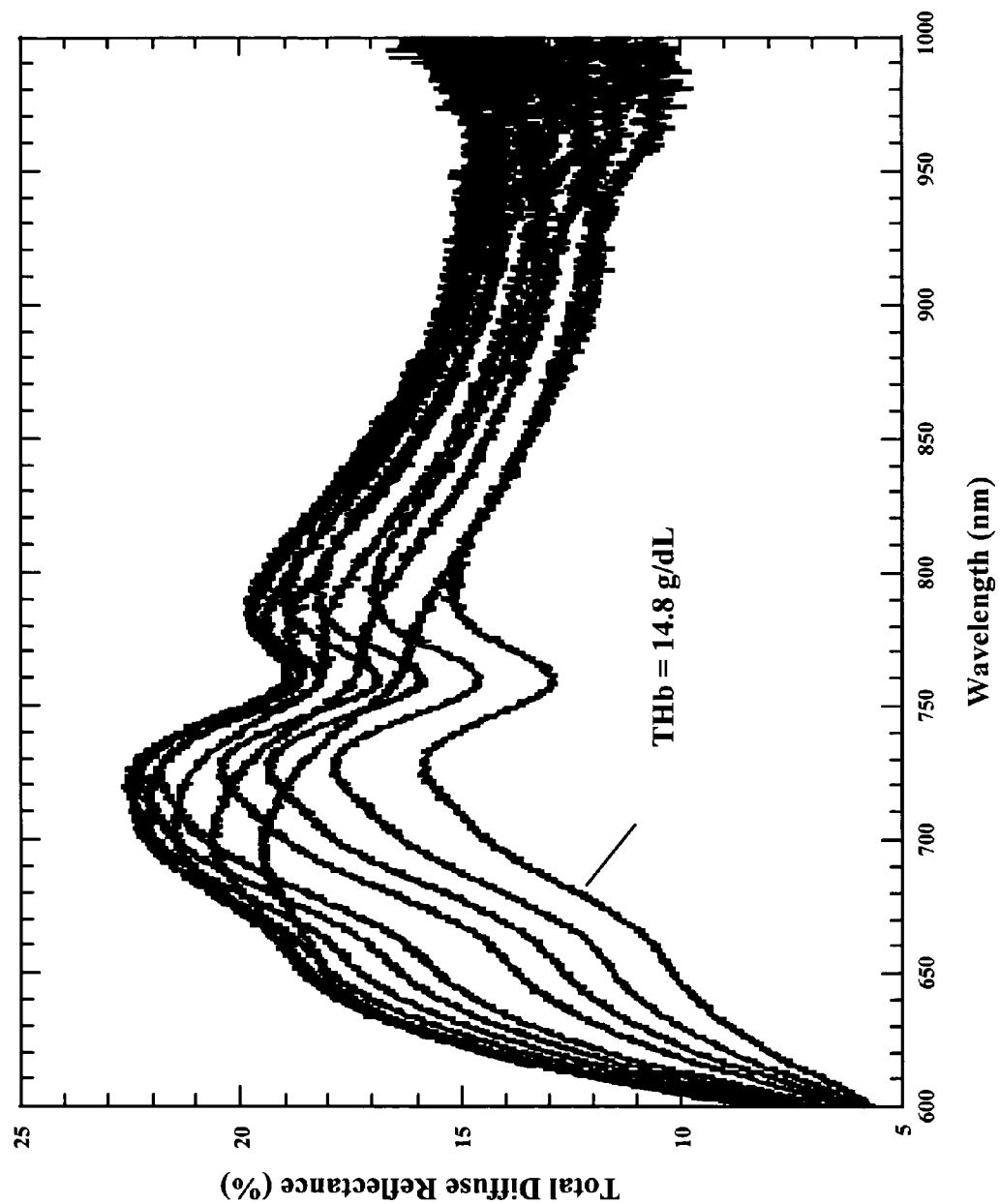
FIGS. 11A-B depict a total diffuse reflectance v.s wavelength from sheep blood for THb 14.8 g/dL.
Figure 11B:
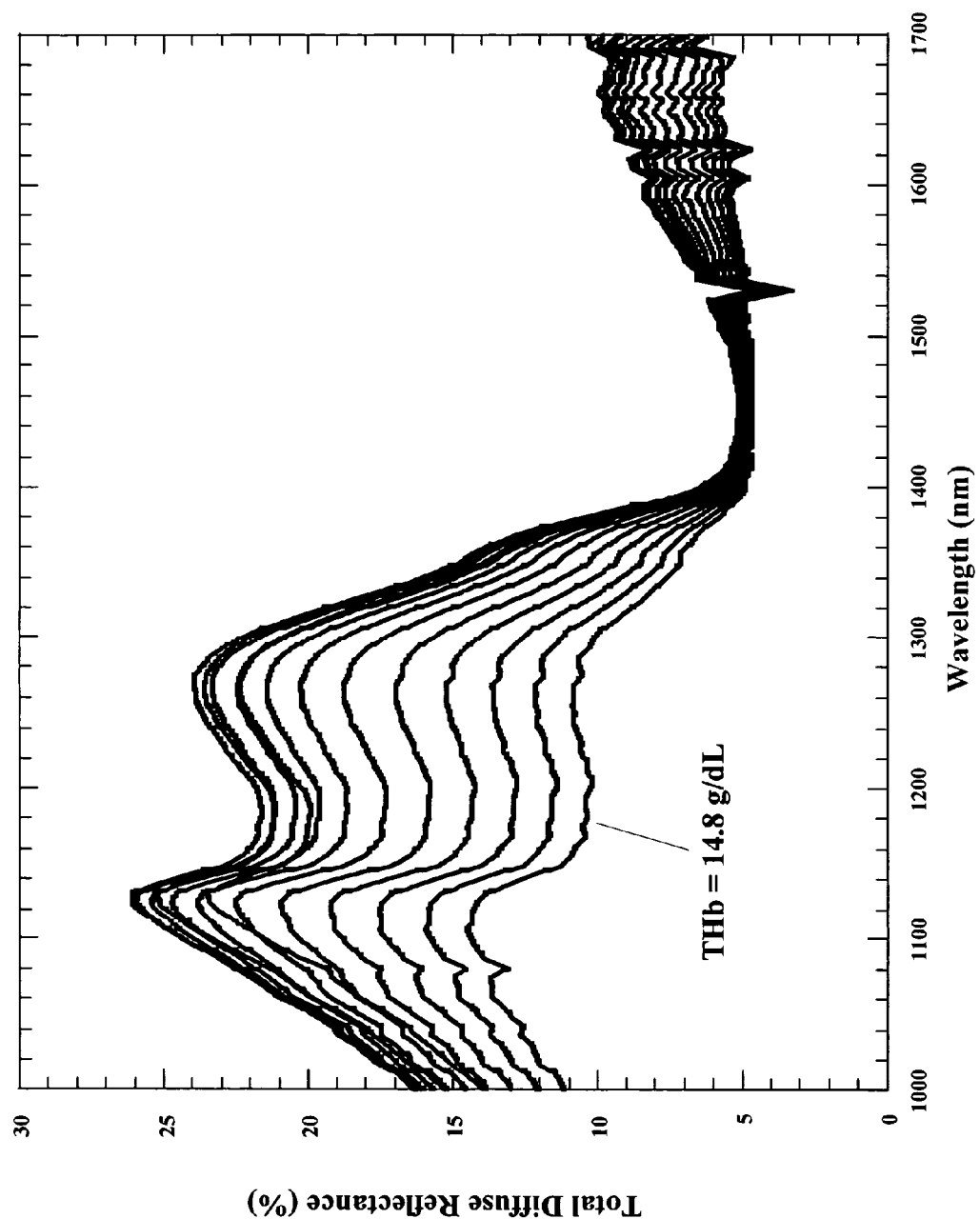

We used a probe with one 0.4-mm fiber for illumination and six 0.4-mm fibers around it for detection. Same blood samples that we used in the studies with the integrating sphere were irradiated in a plastic cuvette (blood volume 0.3 mL; thickness—4 mm) through a thin plastic film (thickness—0.13 mm) simulating thin tissue between the vein and the surface of the underside of the tongue. FIG. 11A shows the dependence of the reflectance signal at 790 and 1300 nm vs. THb that is similar to $R_d$ vs. THb at the two isosbestic wavelengths (805 and 1300 nm). Although the dependence of the ratio R(1300 nm)/R(790 nm) vs. THb is not linear as shown in FIG. 11B, it can be used for calibration of the system. The dependence is not linear because of the following two reasons: the detection fibers collect light scattered almost backward (not in all directions as in the case of the integrating sphere) and 790 nm is not exactly at the isobestic point.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. An apparatus for noninvasive blood analysis comprising:
    right side and left side sections adapted to engage one or more teeth on each of a right side and left side of a patient's jaw,
    two transition sections extending downwardly from each of the side sections,
    a middle section interposed between the two transition sections adapted to be proximate to or in contact with an underside of a patient's tongue, where the middle section includes;
        a emitter, and
        a receiver,
        where the emitter and the receiver are adapted to be proximate or in contact with a surface of a tissue over a big vein associated with an underside of the patient's tongue;
    a light generation/delivery system including a light source capable of generating at least one frequency of light, and a light conduit interconnecting the light source with a radiation outlet, where the system is adapted to deliver radiation to blood in the big vein; and
    a detector/analyzer system including a detector adapted to detect a response from the irradiated blood via a response inlet and an analyzer adapted to convert the detected response into a concentration of a blood component and/or a value of a parameter of the blood.

2. The apparatus of claim 1, further comprising:
    a plurality of emitters and receivers, located in pairs on a right hand side and a left side of the middle section.

3. The apparatus of claim 1, further comprising:
    a display adapted to display the response, the concentration, and/or the value.

4. The apparatus of claim 1, wherein the wavelength of the radiation is from about 200 nanometers to about 20 microns.

5. The apparatus of claim 1, wherein the radiation comprises a plurality of wavelengths or frequencies.

6. The apparatus of claim 1, wherein the detector is capable of detecting data derived from one or a combination of techniques selected from the group consisting of reflectance technique, confocal technique, scanning confocal technique, polarization techniques, interferometry, optoacoustics, low coherence interferometry and reflectometry, techniques based on speckle measurements, fluorescence technique, Raman scattering technique, and two ormulti-photon techniques.

7. The apparatus of claim 1, wherein the response corresponds to hemoglobin and the wavelength is selected from the group consisting of 548 nm, 568 nm, 587 nm, 805 nm, from about 400 nm to about 640 nm and from about 1120 nm to about 1130 nm.

8. The apparatus of claim 1, wherein the blood component is selected from the group consisting of hematocrit, hemoglobin, glycosylated hemoglobin, hemoglobin and glycosylated hemoglobin, glucose, cholesterol, oxy-hemoglobin, deoxy-hemoglobin, and carboxy-hemoglobin.

9. The apparatus of claim 1, wherein the blood component is an exogenous substance selected from the group consisting of a drug, a dye or other reporter in molecular state or a particle made of liquid, gas, or solid material including polymer, metal, semiconductor, dielectric, or a combination of liquid, gas, or solid materials, and a layered structure.

10. The apparatus of claim 9, wherein the exogenous substance is selected from the group consisting of indocyanine green and Evans blue.

11. The apparatus of claim 9, wherein the exogenous substance are particles having a size from about 0.1 nanometer to about 10 microns.

12. The apparatus of claim 1, wherein the radiation is selected from the group consisting of microwave radiation, radio frequency radiation, ultrasound radiation, and low-frequency electromagnetic radiation.

13. The apparatus of claim 1, further comprising:
    a device for generating a static electric or magnetic field.

* * * * *